United States Patent [19]

Andersson et al.

[11] Patent Number: 4,651,566

[45] Date of Patent: Mar. 24, 1987

[54] PORTABLE IMPEDANCE METER FOR NON-DESTRUCTIVE TESTING OF SOUND ABSORBING PANELS

[75] Inventors: Anders O. Andersson, Seattle; David R. Slotboom, Mercer Island; Paul C. Topness, Renton, all of Wash.

[73] Assignee: The Boeing Company, Seattle, Wash.

[21] Appl. No.: 856,705

[22] Filed: Apr. 28, 1986

[51] Int. Cl.$^4$ .............................................. G01N 29/04
[52] U.S. Cl. ........................................ 73/589; 73/583; 73/584
[58] Field of Search ................. 73/589, 583, 572, 643, 73/584

[56] References Cited

U.S. PATENT DOCUMENTS

| | | | |
|---|---|---|---|
| 1,816,917 | 8/1931 | Smythe et al. | 73/589 |
| 2,394,461 | 2/1946 | Mason | 73/104 |
| 2,981,096 | 4/1961 | Carrell | 73/589 |
| 3,019,637 | 2/1962 | Cook et al. | 73/628 |
| 3,508,436 | 4/1970 | Krautkramer | 73/637 |
| 3,658,147 | 4/1972 | Ho et al. | 73/647 |
| 3,809,607 | 5/1974 | Murray et al. | 73/623 |
| 3,844,165 | 10/1974 | Savoy | 73/637 |
| 3,882,848 | 5/1975 | Klar et al. | 73/589 |
| 3,883,841 | 5/1975 | Norel et al. | 73/589 |
| 3,929,007 | 12/1975 | Dent et al. | 73/637 |
| 4,011,750 | 3/1977 | Robinson | 73/628 |
| 4,039,767 | 8/1977 | Leschek | 179/175.1 |
| 4,131,018 | 12/1978 | Muller et al. | 73/432 R |
| 4,249,422 | 2/1981 | Gaunaurd et al. | 73/589 |
| 4,283,953 | 8/1981 | Plona | 73/589 |
| 4,305,295 | 12/1981 | Andersson et al. | 73/589 |

FOREIGN PATENT DOCUMENTS 1303518  5/1971  United Kingdom .

Primary Examiner—Anthony V. Ciarlante
Attorney, Agent, or Firm—Bruce A. Kaser

[57] ABSTRACT

A portable acoustic impedance measuring device 10 is provided for measuring the impedance properties of a panel 12. The device 10 includes a horn section 14 having a flexible plate 18. The plate 18 can assume the curvature of the duct panel 12. The horn section 14 is supported adjacent the panel's surface by a spindle shaft 28 which spans or bridges the inside diameter of the duct 12. The curvature of the plate 18 may be locked to hold the curvature of any of a variety of different panels having various sizes and shapes.

6 Claims, 5 Drawing Figures

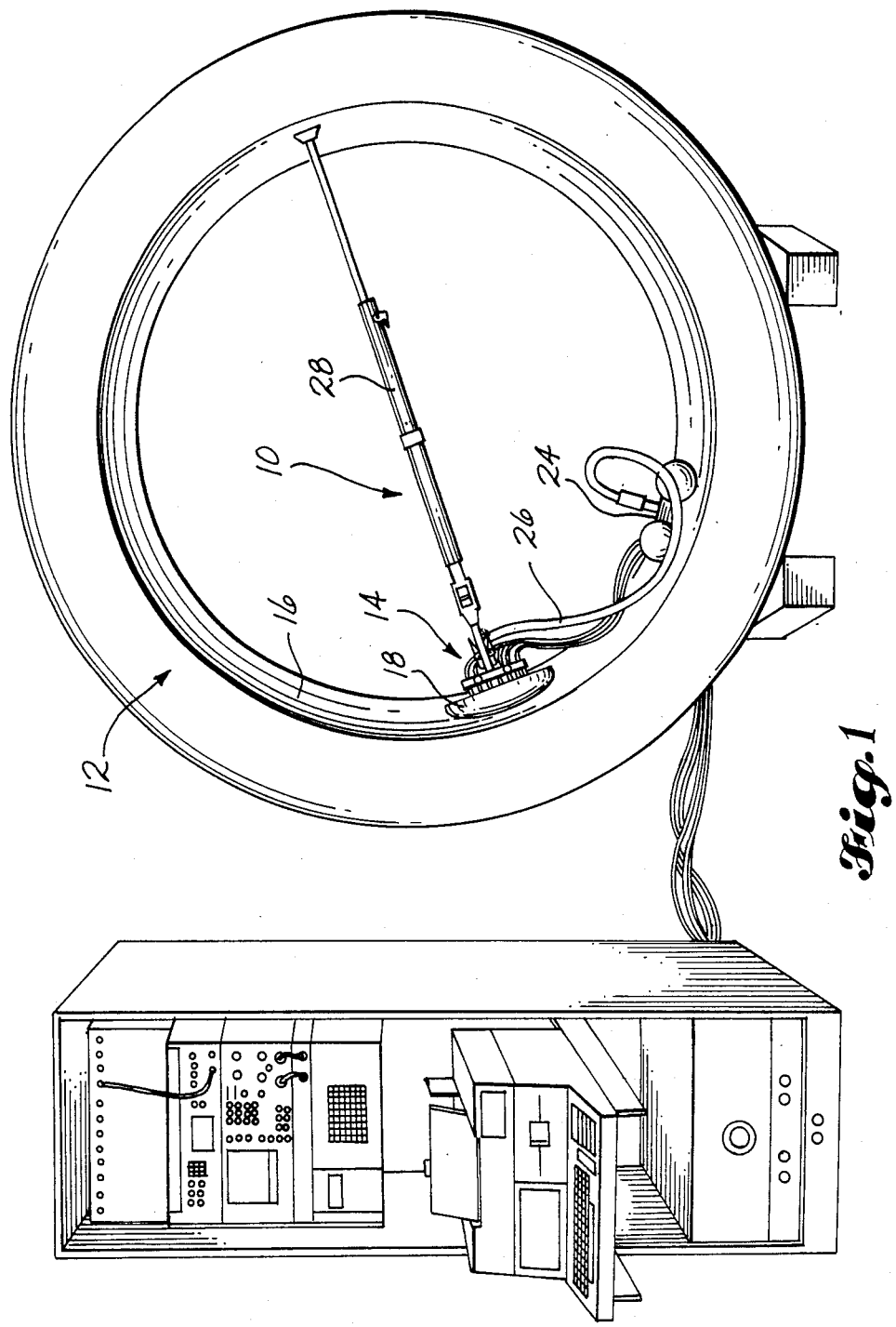

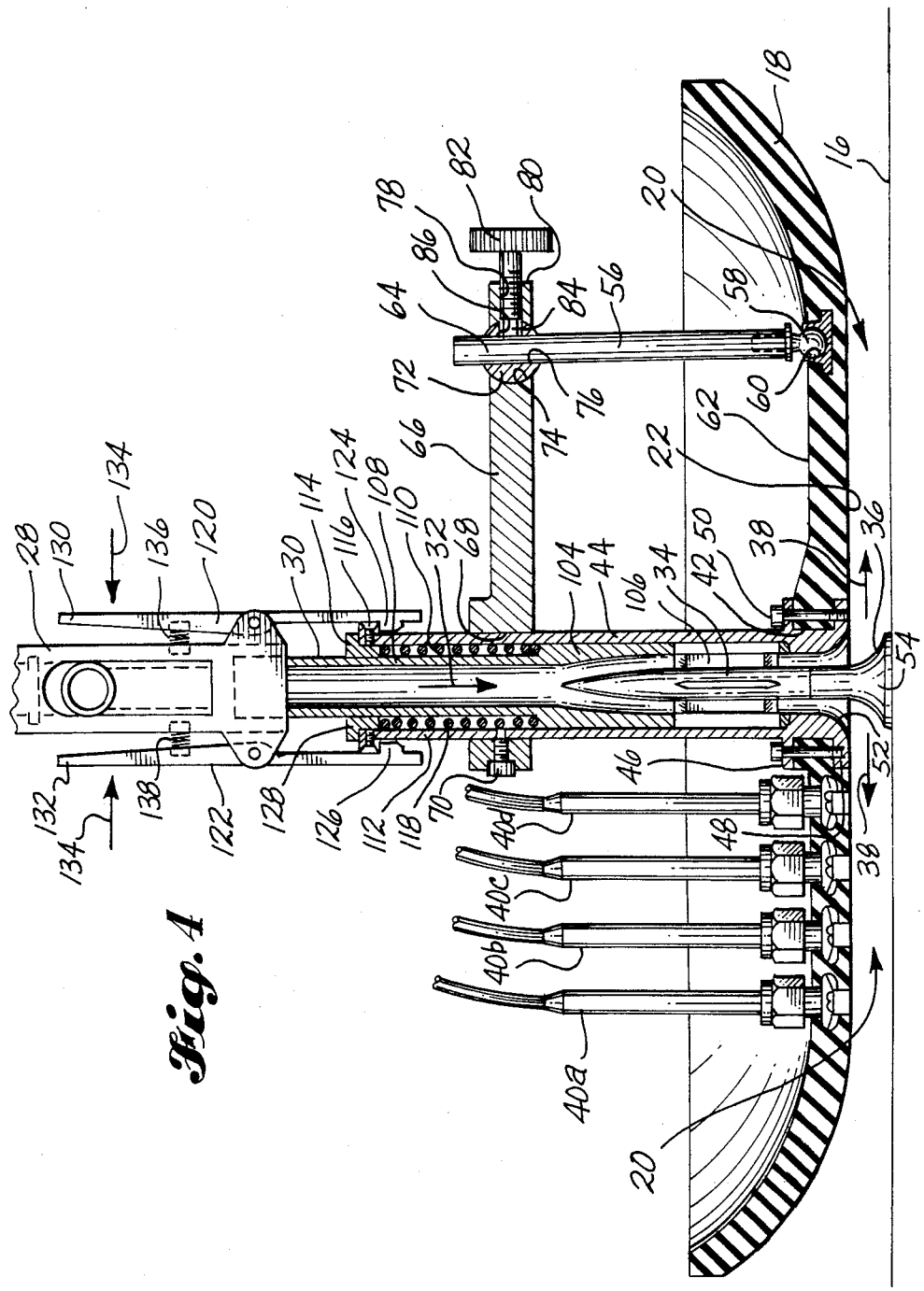

PORTABLE IMPEDANCE METER FOR NON-DESTRUCTIVE TESTING OF SOUND ABSORBING PANELS

DESCRIPTION

1. Technical Field

This invention relates to an apparatus for measuring sound impedance, and more particularly, an apparatus for measuring the sound impedance characteristics or properties of curved sound absorbing panels. This invention is particularly applicable to sound absorbing panels which are intalled in the engine ducts of commercial jet aircraft.

2. Background Art

The invention represents an advance in technology over a portable apparatus for measuring acoustic impedance which was previously disclosed and patented in U.S. Pat. No. 4,305,295, issued to Andersson et al. on Dec. 15, 1981. The main use of the Andersson apparatus was to provide a means for measuring acoustic impedance of panels as assembled, instead of making such measurements from cut samples of the panels. The present invention has the same purpose, i.e., non-destructive testing of panels.

Further, many airports have rules setting limitations on the maximum noise that can be emitted by jet aircraft engines. For this reason, sound absorbing or acoustic panels are typically installed inside the engine ducts of most commercial aircraft. The acoustic panels, hereafter duct panels, are generally cylindrical in shape so as to conform to the shape of an engine duct, and are typically made of a honeycomb material with a perforated material face sheet.

Over a period of time, the sound impedance properties of a typical duct panel degrade because of dirt accumulation or other factors. This results in a lessening of the panel's ability to impede sound and reduce engine noise. Because of the above-mentioned airport rules, it is therefore necessary to periodically test duct panels for sound impedance degradation, and to replace or clean a particular panel if it is no longer impeding sound to a sufficient degree.

Prior to the invention of the portable impedance apparatus disclosed by Andersson in U.S. Pat. No. 4,305,295, destructive testing techniques were used to determine panel impedance properties. As was explained in the Andersson patent, such testing usually involved cutting a sample from a panel and testing it in what is commonly known as an impedance tube. A problem associated with such method was that it did not permit quality control of duct panels while they were installed in engine ducts.

The ideal situation is to test a panel while it is in an assembled condition without need of removing and/or destroying a portion of the panel, or all of it. The purpose of Andersson, therefore, was to provide a portable impedance meter which could non-destructively test a duct panel. The present invention has the same function and purpose as Andersson, but provides hardware improvements thereover.

3. Disclosure of the Invention

The present invention provides a portable apparatus which can be placed and fixed in position inside a jet engine duct to measure the sound impedance properties or characteristics of a duct panel.

The invention includes a plate-like or horn member having a flexible surface which can assume the curvature of the surface of the duct panel. The horn member is first placed against the panel surface to assume the curvature thereof. The horn member is then locked into that curvature followed by spacing the member a certain preselected distance from the panel surface. The member's panel-facing surface maintains the panel's curvature, and a channel of uniform width or thickness is thereby formed between the facing surfaces of the panel and the horn member, which is used for transmitting sound therethrough.

The horn member is connected to a spindle shaft in a manner so that the member can move back and forth on the spindle shaft, from a position contacting the panel surface to the above-described position spaced from the panel. Preferably, the horn member includes a bore in a central portion thereof through which the spindle shaft extends. A tubular guide sleeve member is connected to the bore extending rearwardly therefrom and in sliding contact with the spindle shaft, so that the horn member can be moved. Both the guide sleeve and the bore structurally cooperate with each other to form a sleeve passageway in which the spindle shaft is received. The spindle shaft has an end portion which is normally received inside this passageway when the surface of the horn member is in contact with the panel surface. When the horn member is spaced from the panel, to form the channel, the end portion of the spindle shaft then projects or extends outwardly from the passageway, to thereby support the horn member and to define the distance of the spacing of the member from the panel.

In accordance with an aspect of the invention, the spindle shaft may extend telescopically to bridge the diameter of the duct panel. The previously mentioned end portion of the spindle shaft, which is adjacent the horn member, contacts one side of the panel, and another telescoping end portion contacts the other side. A spring device may be centrally located in the shaft and biased to place a certain force on each end, thereby holding the shaft and horn member in place inside the duct panel.

A plurality of stiff surface-shaping struts are used to lock the flexible surface of the horn member into the same curvature as the panel surface. Each strut is in the form of a generally elongated rod. A strut support member or plate is connected to the guide sleeve and projects radially outwardly from the guide member aft of the horn member. One end of each strut is coupled to the aft side of the horn member, and the other end is connected to the strut support plate. More specifically, the first end is pivotally coupled to the horn member, and the other end of each strut is coupled to the support plate in a manner so that each strut can move relative to the support plate, in correspondence with changes in curvature of the horn member as it assumes the curvature of the panel surface. When such curavture is assumed, however, each strut is fixedly connected to the support plate to lock the shape of the horn member.

Preferably, that end of each struct which is connected to the horn member includes a ball-shaped portion which is received in a socket located on the aft side of the horn member. Each strut is coupled to the strut support plate by a generally spherically-shaped gimbal member that is received within a portion of the support plate. The gimbal member includes a first bore that provides a passageway through which the strut extends. The strut support plate also has a threaded bore that extends radially outwardly from the position of the gimbal member in the plate to an outer radial edge of the plate. A thumb wheel screw is received within this threaded bore, in a manner so that the thum wheel screw can be screwed inwardly and outwardly therein.

The gimbal member also has a second bore oriented generally perpendicularly to the first bore. The second bore is configured so that it provides a passageway from the threaded bore in the support plate into the first bore of the gimbal member. This second bore is of a sufficient width so that the end of the thumb wheel screw may extend through the second bore and contact the strut extending through the first bore. Tightening or screwing the thumb wheel screw inwardly can therefore cause the thumb wheel screw to hold the strut in a fixed position. This is done, of course, to lock the shape or curvature of the horn member in place. Prior to placement of the horn member in contacting relationship with the panel surface, the thumb wheel screw is loosened or screwed outwardly permitting free movement of the strut inside the first bore of the gimbal member.

The spindle shaft includes a hollow tubular portion or section to which the horn member is attached, and through which generated sound waves are transmitted into the channel. These sound waves are used to measure the impedance properties of the panel. The spindle shaft's hollow tubular portion has an outer sidewall portion that is in sliding contact with an inner sidewall portion of the guide sleeve, to permit movement of the horn member relative to the spindle shaft. However, another outer sidewall portion of the spindle's tubular portion, and another inner sidewall portion of the guide sleeve define a cylindrical space in which a spring is received. The spring couples the guide sleeve to the shaft's tubular portion, and is biased for moving the guide sleeve (and the horn member connected thereto) away from the surface of the panel. A means is provided for holding the horn member against the panel surface and against the bias of the spring. Such holding means is releasable for permitting the spring to move the horn member away from the panel.

A plurality of microphones are mounted to the horn member for sensing the above-mentioned generated sound waves as they are transmitted through the channel. The microphones are used to measure the amplitude and phase of the sound waves and to provide data signals indicative thereof. A computerized control system processes the signals from the microphones and makes a determination of panel sound impedance therefrom.

The invention is designed to be used in connection with the invention disclosed in the above-cited Andersson patent, U.S. Pat. No. 4,305,295. The invention provides certain hardware improvements over and above the hardware disclosed in the Andersson patent, both with regard to the portable impedance meter and the sound generation system and controls therefore. An advantage to the present invention is that it is better adapted for use in connection with duct linings already installed in aircraft engines. It is conceivable, for example, that the invention could be used to test a duct panel in an engine as a jet aircraft is being serviced on an airfield tarmac.

BRIEF DESCRIPTION OF THE DRAWINGS

In the drawings, like reference numerals and letters refer to like parts throughout the various views, and wherein:

FIG. 1 is a pictorial view showing a portable sound impedance meter constructed in accordance with a preferred embodiment of the invention, and in operative use positioned inside a cylindrical duct panel which would normally line the intake duct of an aircraft engine;

FIG. 4 is a cross-sectional view of the horn section shown in FIGS. 2 and 3, and is taken along the center line thereof.

BEST MODE FOR CARRYING OUT THE INVENTION

Figure 3:
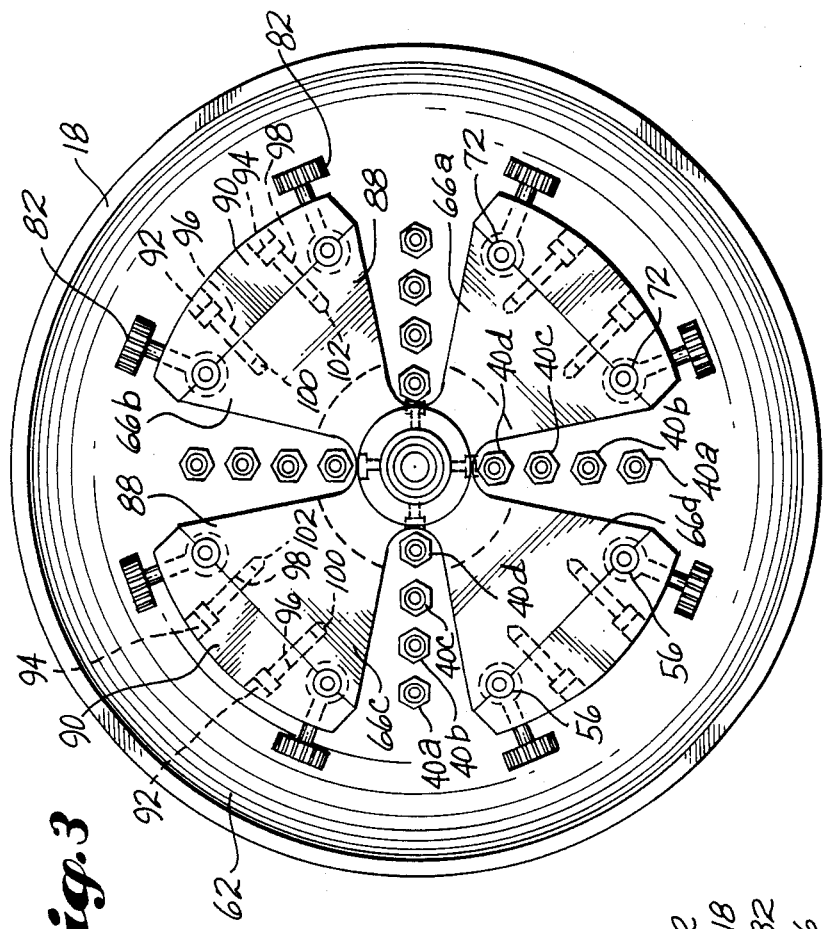
FIG. 3 is a top plan view of the horn section shown in FIG. 2.

Referring now to the drawings, and first to FIG. 1, therein is shown a portable impedance meter 10 constructed in accordance with a preferred embodiment of the invention. The meter 10 is shown in a position bridging the diameter of a cylindrical duct panel 12. Normally, the duct panel 12 would be located inside the duct of a jet aircraft engine. The panel 12 shown in FIG. 1 represents a test mock-up of this situation.

The impedance meter 10 has a horn section 14 which is positioned adjacent the inside surface 16 of the panel 12. The horn section 14 is made of a flexible plate-like member or plate 18 consisting of silicon rubber, for example. The flexible plate 18 is shapable to generally assume the curvature of the panel surface 16 when it is placed in contact with such surface. When the device 10 is in use, the plate 18 is spaced a certain preselected distance from the surface 16. This is shown in FIG. 4.

The horn section 14 is connected to a cluster of sound drivers 24 by means of a flexible tubing 26. The horn section 14 is supported adjacent the panel surface 16 by a telescoping spindle shaft 28 which spans the inside diameter of the panel 12. The tubing 26 is connected to a hollow tubular portion 30 of the spindle shaft, which is located in the horn section 14. The sound generators 24 generate sound waves which are piped through the flexible tubing 26 into this hollow tubular portion 30, in the direction indicated by arrow 32.

The spindle shaft 28 has an end portion 34 which supports the horn section 14 next to the panel surface 16. The end portion 34 has a generally conically-shaped diffuser portion 36 which directs the generated sound waves outwardly through the channel 20, in the direction indicated by arrows 38. As the sound travels outwardly, a plurality of microphones 40A, 40B, 40C, 40D provide signals which are processed, in a manner to be described later, to determine the sound impedance of the duct panel 12. In preferred form, a total of 16 microphones 40A, 40B, 40C, 40D are connected to the plate in the manner shown in FIGS. 2 and 3. Four banks of four microphones each extend radially outwardly from the center of the plate 18. Each bank extends perpendicularly to each adjacent bank.

The operation of the present invention is in most respects similar to the operation of the sound impedance testing device which was disclosed in the above-referenced Andersson patent (U.S. Pat. No. 4,305,295). For example, the microphones 40A–40D are responsive to acoustic pressure resulting from sound waves traveling radially outwardly through the channel 20. Signals from the microphones 40A–40D are processed in the manner disclosed in the Andersson patent to determine impedance properties.

As shown in the drawings, the plate 18 has radial symmetry about a carrier line defined by the spindle 28. The plate 18 includes a central bore 42 to which is connected a hollow guide sleeve or guide member 42. The guide sleeve 42 is connected to the plate 18 by means of a pair of radially projecting flanges 46, 48 having a space therebetween in which the edge of the bore 42 is received. A plurality of screws 50 extend through the flanges 46, 48 and that portion of the plate 18 which is near the edge of the bore 42. These screws 50 firmly connect the plate 18 to the guide sleeve 44.

The guide sleeve 44 is in sliding contact with the hollow tubular portion 30 of the spindle shaft 28. Sliding the guide sleeve 44 relative to the spindle shaft 28, moves the horn section 14 back and forth thereby permitting movement of the panel facing surface 22 of the plate 18 from a position next to the panel surface 16 to a position spaced therefrom.

When the device 10 is to be used for measuring the impedance of the panel 12, the device 10 is first placed inside the panel in the position shown in FIG. 1. Initially, the guide sleeve 44 of the horn section is moved downwardly relative to the conically shaped end portion 34 of the spindle shaft 28. The guide sleeve 44 has an end throat portion 52 which communicates sound from the hollow tubular portion 30 into the channel 20. This throat portion 52 is shaped for complementary fitment to the conically-shaped diffuser 36 portion of the spindle shaft 28. Therefore, when the device 10 is first placed inside the panel 12, the end portion 52 of the guide sleeve 44 is mated to the diffuser portion 36 of the spindle shaft's end 34. At this time, the surface 54 of the diffuser portion 36, which contacts the surface 16 of the panel, is substantially flush with the plate's panel-facing surface 22. The curvature of the plate 18, and more specifically, the curvature of the plate's flexible surface 22, is maintained by a plurality of surface-shaping struts 56. Eight surface-shaping struts 56 are distributed symmetrically an equal distance from and around the spindle shaft 28. Each strut 56 has a ball-shaped end portion 58 which is received in a socket 60 connected to the aft side or surface 62 of the plate 18. The other end 64 of each strut 56 is connected to a radially projecting strut support member or plate 66.

Figure 2:
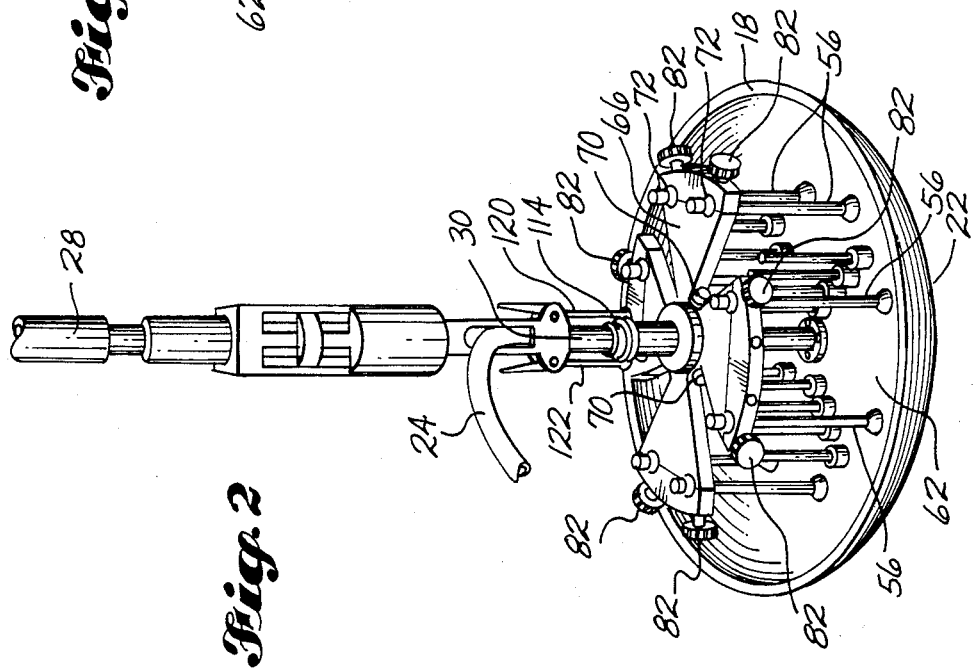
FIG. 2 is a pictorial view of the left end or horn section of the impedance meter shown in FIG. 1.

In preferred form, and referring now to FIGS. 2 and 3, the support member 66 is generally in the shape of a four-leaf clover. The support member 66 has a centrally located bore 68 through which extends the spindle shaft 28. The support member 66 is connected to the guide sleeve 44 by means of four screws 70. Each leaf 66A, 66B, 66C, and 66D, of the support member 66 is connected to a pair of surface-shaping struts 56. Such connection is made by means of a plurality of spherically shaped gimbal members 72, which are received in the support member 66. One gimbal member 72 is provided for each surface-shaping strut 56. Each gimbal member 72 is pivotally seated in a spherically shaped socket 74, in the support member 66.

Each gimbal member 72 has a first bore 76 through which extends the other end 64 of each strut 56. A threaded bore 78 projects radially outwardly from the gimbal member 72, to the outer radial edge 80 of the support member 66. A thumbwheel screw 82 is threaded therein and has an end portion 84 extending through a second bore 86 in the gimbal member 72.

When the plate 18 is placed adjacent the panel surface 16, the thumbwheel screws 82 for each strut 56 are first screwed outwardly beforehand, to loosen them. This permits the ends of the struts 64 to move or slide through the first bore 86 in each gimbal member 72, in correspondence with movement of the plate 18 as its surface 22 assumes the curvature of the panel surface 16. Once this is done, the thumbwheel screws are then tightened so that the ends 84 of the screws abut adjacent the end 64 of each strut 56, thus holding the struts in place. When the plate 18 is then spaced from the panel surface 16, the plate's panel facing surface 22 will maintain the curvature of the panel, since the struts 56 are constrained from further movement.

In preferred form, each leaf 66A, 66B, 66C and 66D of the support member 66 are made of metal and have an inner portion 88 and an outer portion 90. The outer portion is connected to the inner portion by means of screws 92, 94, which extend through bores 96, 98 in the outer portion 90, and are threaded into bores 100, 102 in the inner portion 88. This is preferred construction because it facilitates milling of the spherical sockets 74 which seat each gimbal member 72.

As mentioned previously, the guide sleeve 44 is in sliding contact with the tubular portion 30 of the spindle shaft 28. In preferred form, the tubular portion 30 has a lower portion 104 that has an outer diameter substantially equal to the inner diameter of the guide sleeve 44. This lower portion 104 is connected to the end portion 34 of the spindle shaft by means of four brackets 106 which are distributed around the circumference of the shaft's end 34. This type of connection provides air spaces between the brackets 106 and through which generated sound is transmitted into the channel 20.

The shaft's tubular portion 30 also has an upper portion 108 whose outer diameter is less than the inner diameter of the guide sleeve 44. This construction defines a hollow cylindrical space 110. A collar 114 is connected by means of a plurality of set screws 116 to an upper portion 112 of the guide sleeve. A spring 118 is positioned in this space 110 and is biased to move the guide sleeve 44 upwardly for spacing the horn section 14 from the panel surface 16. Normally, when the plate 18 is first placed adjacent the panel surface 16, the spring 118 is in a compressed condition and is held in comparison by a pair of movable locking members 120, 122.

The locking members 120, 122 have flanges 124, 126 which are latched onto the top surface 128 of the collar 114. Each locking member 120, 122 is pivotally connected to the spindle shaft 28. Pushing the ends 130, 132 of the locking members 120, 122 inwardly in the direction indicated by arrows 134 releases the spring 118 and causes the horn section 14 to be spaced from the panel surface 16. A pair of springs 136, 138 normally push the ends 130, 132 of the locking members 120, 122 outwardly. In preferred form, to best measure impedance properties, the plate 18 is spaced approximately one half inch from the panel surface 16.

The spindle shaft 28 telescopes so that the device 10 is adjustable for placement inside duct panels 12 of various diameters. A suitable spring device or mechanism may be placed in the body of the shaft, centrally located, so that each end of the shaft 28 pushes against the panel surface 16 with a certain predetermined pressure. Such pressure need only be sufficient to hold the device 10 in place so that it will not move when the impedance of the panel is being measured.

Figure 5:
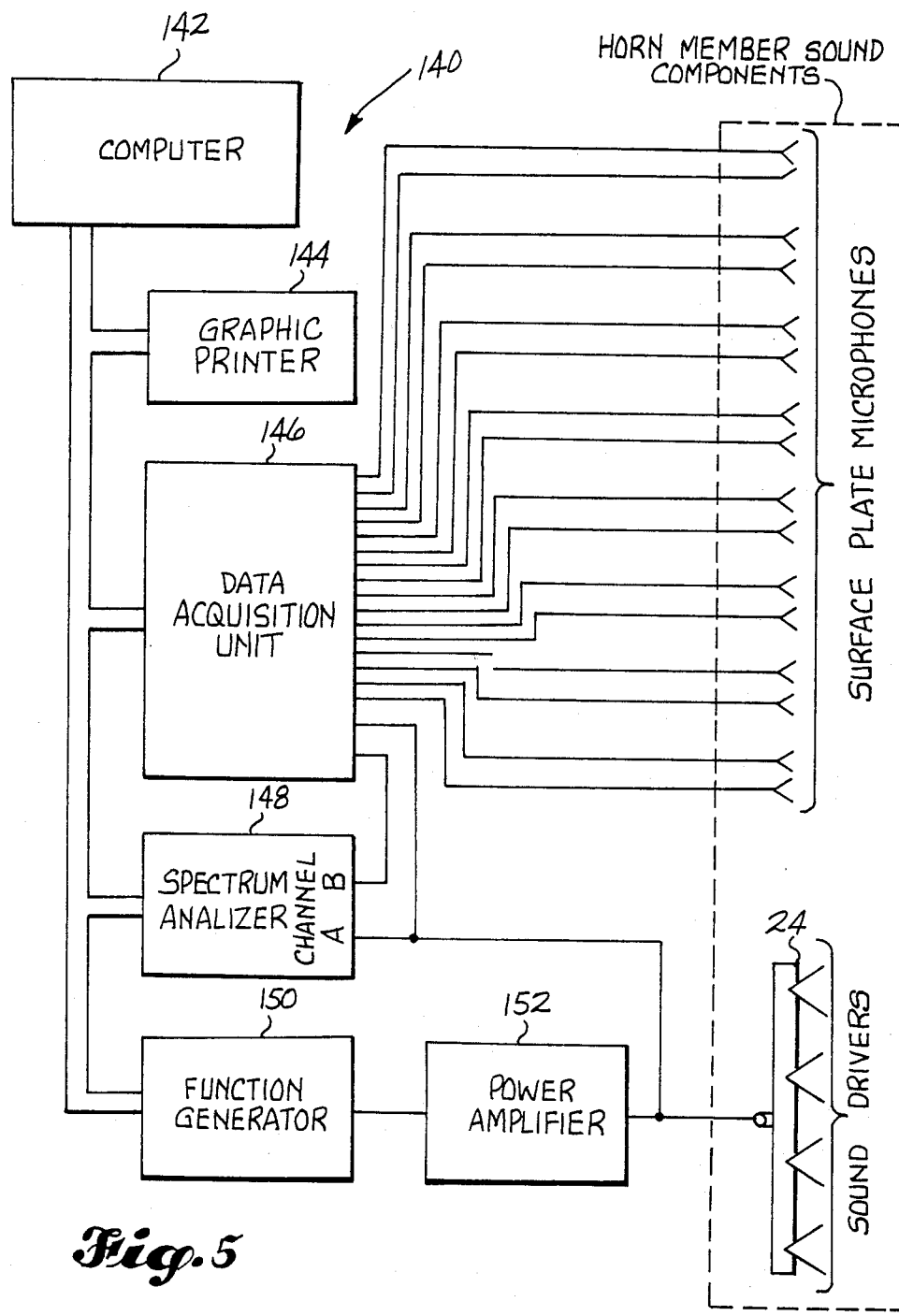
FIG. 5 is a schematic drawing of the sound generation, sound receiving, and signal processing system of the invention which is used in connection with the horn section shown in FIGS. 2–4 to measure sound impedance of a duct panel.

The device 10 is used in conjunction with a completely automatic sound generating and data acquisition system 140, which is shown in FIG. 5. The system 140 automatically generates steady state sound waves which are transmitted from the sound drivers 24 through the flexible tubing 26 into the horn section 14. The sound waves are then sent outwardly through the channel 20 and the resultant pressure field in the channel 20 is measured by the microphone in the plate 18.

A computer 142 controls sound wave generation and data acquisition. By way of example only, a Hewlett Packard 9826 computer would be suitable for use in praticing the invention. The computer 142 is operatively connected to a graphic printer 144, a data acquisition unit 146, a spectrum analyzer 148, and a wave function generator 150. A suitable graphic printer for use in practicing the invention would be a Hewlett Packard 2671G graphic printer; a suitable data acquisition unit 146 would be a Hewlett Packard 3497A data acquisition/control unit; a suitable spectrum analyzer would be a Hewlett Packard 3582A spectrum analyzer; and a suitable wave function generator would be a Hewlett Packard 3325A synthesizer/function generator.

The computer 142 is programmed such that it causes the wave function generator to generate an electric sine wave signal of a certain specified or preselected frequency so that sound waves having a certain desired pressure level will be generated in the channel 20. This signal is transmitted to and amplified by a power amplifier 152, and it is then transmitted onwardly to the cluster of sound drivers 24 which actually generate the sound waves. In preferred form, the sound drivers consist of four JBL 2410 sound drivers. The sound waves are transmitted into the horn section 14, and one of the mid radius microphones in the plate 18 is used to measure the pressure level of the sound waves. If the measured level is not the same as the desired level, a correction is made to the amplitude of the generated electronic sine wave signal. Such correction would be an iterative process controlled by the computer 142 until generated pressure level is approximately the same as the desired pressure level. Since this process is iterative, a safeguard is built into the programming of the computer 142 to ensure that the acoustic drivers 24 are not inadvertently overloaded.

Once the desired sound pressure level is produced in the channel 20, the output signal of each microphone in the plate is measured. These signals are compared by the spectrum analyzer 148 with the input signal sent to the sound drivers. This is done for the purpose of determining both amplitude and phase of the sound waves in the channel 20. Of course, and as a person skilled in the art would realize, the phases of each microphone would be relative. In order to put the amplitude of the sound waves on an absolute basis one of the microphones in the plate must be calibrated. Once the sound field is known, the impedance of the panel 16 can be determined in accordance with the teachings of the Andersson patent.

The best mode for carrying out the invention as described above is provided herein for illustrative purposes only. It is to be understood that certain modifications could be made to the invention without departing from the spirit and scope thereof. Patent protection is to be defined solely by the claims which follow, in accordance with the established doctrines of patent claim interpretation as set forth in the patent law.

What is claimed is:

1. For use in measuring the acoustic impedance of a panel or the like, including a panel having a curved surface, an apparatus comprising:
   a horn member having a flexible surface for assuming a panel surface's curvature;
   spindle means for supporting said horn member adjacent said panel surface, said horn member being movable relative to said spindle means, to move said flexible surface of said horn member from a position in contacting relationship with said panel surface, so that said flexible surface may assume the curvature thereof, to a position spaced from said panel surface; and
   locking means operable to hold said flexible surface in substantially the same curvature as said curvature of said panel surface when said flexible surface is spaced from said panel surface.

2. The apparatus of claim 1, including a hollow tubular guide sleeve member connected to a central portion of said horn member, said guide sleeve member extending rearwardly relative to a bore in said horn member, said guide member and said bore forming a passageway in which is received said spindle means, said spindle means including an end portion, wherein said end portion is received within said passageway when said flexible surface of said horn member is in contacting relationship with said panel surface, and wherein said end portion extends outwardly from said passageway when said flexible surface is spaced from said panel surface, in correspondence with said movement of said horn member relative to said spindle means.

3. The apparatus of claim 2, wherein said locking means includes:
   a plurality of surface-shaping struts each having an elongated body,
   a radially projecting strut support member connected to said guide sleeve member,
   first coupling means for pivotally connecting a first end of each surface-shaping strut to said horn member, in a manner so that each strut may extend aft of said horn member, and
   second coupling means for connecting each strut to said strut support member, wherein said second coupling means permits movement of said struts relative to said strut support member in correspondence with changes in curvature of said flexible surface of said horn member as said flexible surface assumes said curvature of said panel surface, and wherein said second coupling means includes means for fixedly connecting said struts to said strut support member after said flexible surface has assumed said panel surface's curvature.

4. The apparatus of claim 3, wherein said first coupling means comprises a generally ball-shaped portion of said first end of each strut, said ball-shaped portion being received in a socket positioned in said horn member, and wherein said second coupling means comprises for each strut a generally spherically-shaped gimbal member pivotally received within a portion of said strut support member, said gimbal member having a first bore through which extends said strut in a sliding manner, said strut support member having a threaded bore extending from said gimbal member radially outwardly to an outer radial edge of said strut support member, with a thumb wheel screw being received within said threaded bore for screwing inwardly and outwardly therein, said gimbal member further having a second bore oriented generally perpendicularly to said first bore, said second bore providing a passageway from said threaded bore to said first bore, said passageway being of a sufficient width so that the end of said thumb wheel screw may extend through said second bore and contact said strut extending therethrough, to thereby hold said strut in fixed position when said thumb wheel screw is screwed inwardly.

5. The apparatus of claim 4, wherein said spindle means includes a hollow tubular portion having an outer sidewall portion that is in sliding contact with an inner sidewall portion of said guide sleeve member, and wherein another outer sidewall portion of said spindle means tubular portion and another inner sidewall portion of said guide sleeve member define a cylindrical space, with a spring being received in said cylindrical space, said spring coupling said guide member to said spindle means tubular portion and being biased to move said guide member and said horn member connected thereto away from said panel surface, to cause said spindle member end portion to be extended relative to said flexible surface of said horn member, and including means for holding said guide and horn members against the bias of said spring, in a manner so that said flexible surface of said horn member may be held in contacting relationship with said panel surface.

6. The apparatus of claim 5, wherein said spindle means end portion includes a cone-like diffuser portion, and wherein said passageway, which is defined by said bore in said horn member and said guide sleeve member, has an end opening shaped for complimentary fitment with said diffuser portion, and wherein when said diffuser portion is received in said passageway, a panel contacting surface of said diffuser portion is in substantially flush relationship with said flexible surface of said horn member.

* * * * *

UNITED STATES PATENT AND TRADEMARK OFFICE
CERTIFICATE OF CORRECTION

PATENT NO. : 4,651,566

DATED : March 24, 1987

INVENTOR(S) : Anders O. Andersson et al.

It is certified that error appears in the above-identified patent and that said Letters Patent are hereby corrected as shown below:

Column 1, line 14, "intalled" should be -- installed --.

Column 2, line 56, "curavture" should be -- curvature --.

Column 2, line 59, "struct" should be -- strut --.

Column 3, line 3, "thum" should be -- thumb --.

Column 5, line 7, "carrier" should be -- center --.

Column 5, line 40, after "surface 22.", start a new paragraph.

Column 6, line 7, "first bore 86" should be -- first bore 76 --.

Column 6, line 48, "comparison" should be -- compression --.

Signed and Sealed this

Eighth Day of September, 1987

Attest:

DONALD J. QUIGG

Attesting Officer

Commissioner of Patents and Trademarks